(12) United States Patent
Burman et al.

(10) Patent No.: US 6,316,414 B1
(45) Date of Patent: Nov. 13, 2001

(54) SOMATOSTATIN ANALOGS FOR THE TREATMENT OF CANCER

(75) Inventors: Anand C. Burman; Sudhanand Prasad; Rama Mukherjee; Manu Jaggi; Anu T. Singh; Archna Mathur, all of Ghaziabad (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 09/629,371

(22) Filed: Jul. 31, 2000

(51) Int. Cl.[7] .................. A61K 38/00; A61K 38/31; C07K 5/00; C07K 17/00
(52) U.S. Cl. .................. 514/16; 530/300; 530/311; 530/328
(58) Field of Search .................. 514/16; 530/300, 530/311, 328

(56) References Cited

U.S. PATENT DOCUMENTS

| | | | |
|---|---|---|---|
| 4,904,642 | 2/1990 | Coy et al. | 514/11 |
| 5,552,520 | 9/1996 | Kim et al. | 530/311 |
| 5,597,894 | 1/1997 | Coy et al. | 530/311 |
| 5,753,618 | 5/1998 | Cavanak et al. | 514/11 |
| 6,025,372 | 2/2000 | Yang et al. | 514/316 |

FOREIGN PATENT DOCUMENTS

| | | | |
|---|---|---|---|
| 4104308 | 8/1991 | (DE) | A61K/37/02 |
| 0344297 | 5/1994 | (EP) | A61K/37/24 |
| 0309297 | 3/1989 | (EP) | C07K/5/02 |
| 9844921 | 10/1998 | (WO) | A61K/31/395 |
| 9844922 | 10/1998 | (WO) | A61K/31/395 |
| 9922735 | 5/1995 | (WO) | A61K/31/445 |
| 0006185 | 2/0000 | (WO) | A61K/38/00 |
| 9639161 | 12/1996 | (WO) | A61K/38/00 |
| 9845285 | 10/1998 | (WO) | C07D/403/14 |
| 9102745 | 3/1991 | (WO) | C07K/14/575 |

OTHER PUBLICATIONS

H. Frucht et al.; Characterization of Functional Receptors for Gastrointestinal Hormones on Human Colon Cancer Cells; Cancer Research, Mar. 1, 1992; 1114–1122.

K. Frank–Raue et al.; Somatostatin Receptor Imaging in Persistent Medullary Thyroid Carcinoma; Clinical Endocrinology (1995); 31–37.

E. Bombardieri, et al.; Somatostatin Receptor Imaging of Small Cell Lung Cancer (SCLC) by . . . Scintigraphy; European Journal of Cancer; vol. 31A, No. 2, pp. 184–187, 1995.

John T. Pelton et al.; Design and Synthesis of Conformationally Constrained Somatostatin Analogues with High Potency and Specificity for $\mu$ Opioid Receptors; J.Med. Chem. 1986, 29. 2370–2375.

K. Gulya, et al.; Cyclic Somatostatin Octapeptide Analogues with High Affinity and Selectivity Toward MU Opioid Receptors; Life Sciences, vol. 38, pp. 2221–2229.

M. Brown et al.; Somatostatin: Analogs with Selected Biological Activities; Science vol. 196; Jun. 1977; pp. 1467–1469.

Pinski, J. et al.; Int. J. Cancer, 57, 574–580 (1994).

M.L. Sautter–Bihl et al.; Somatostatin Receptor Imaging: A New Horizon . . . Neuroblastoma; Seminars in Oncology 2003–2007; vol. 21, No. 5, Suppl 13 (Oct.), 1994; pp38–41.

Liebow, et al.; Somatostatin Analogues Inhibit Growth of Pancreatic Cancer . . . Phosphatase; Proc. of Nat. Acad of Sciences of USA; 1989, 86(6) p. 200.

The Effects of the Somatostatin Analog Octreotide on Angionenesis in Vitro; Romano Danesai and Mario Del Tacca.

Somatostatin Analogues Inhibit . . . Membrane; Woltering et al;—of Surgical Research; 50; 245–251 (1991).

*Primary Examiner*—Avis M. Davenport
(74) *Attorney, Agent, or Firm*—Ladas & Parry

(57) ABSTRACT

The present invention encompasses novel peptides that are agonists to somatostatin and the use of the agonists for treatment of cancer. The invention particularly relates to the design and synthesis of novel analogs of somatostatin incorporating $\alpha$, $\alpha$-dialkylated amino acids in a site specific manner. The invention encompasses methods for the generation of these peptides, compositions containing the peptides and the pharmacological applications of these peptides especially in the treatment and prevention of cancer.

26 Claims, 1 Drawing Sheet

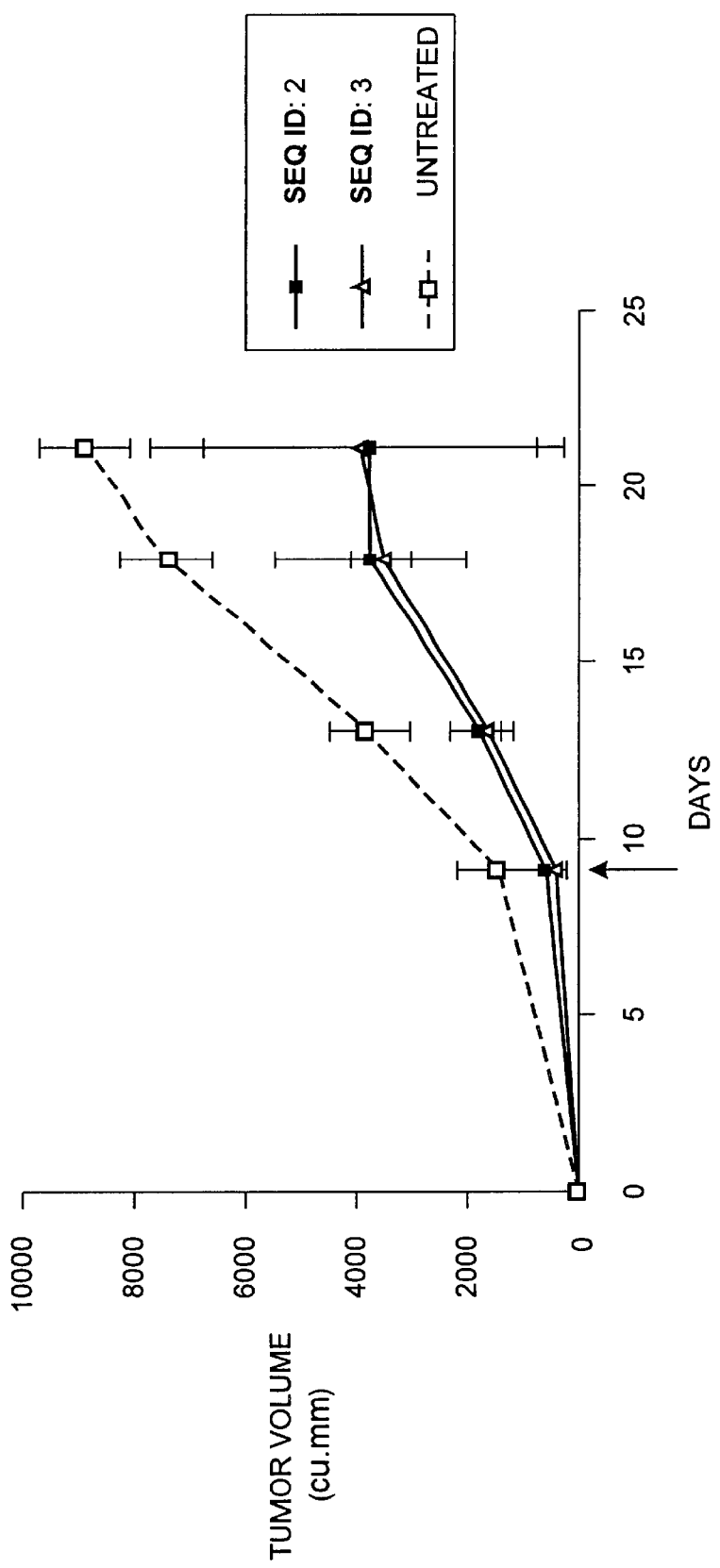
F I G. 1

SOMATOSTATIN ANALOGS FOR THE TREATMENT OF CANCER

FIELD OF INVENTION

The present invention encompasses novel peptides that are agonists to somatostatin and the use of the agonists for treatment of cancer. The invention particularly relates to the design and synthesis of novel analogs of somatostatin incorporating α, α-dialkylated amino acids in a site specific manner. The invention encompasses methods for the generation of these peptides, compositions containing the peptides and the pharmacological applications of these peptides especially in the treatment and prevention of cancer.

BACKGROUND OF THE INVENTION

Somatostatin (SST) is a widely distributed peptide occurring in two forms SST-14 (with 14 amino acids) and SST-28 (with 28 amino acids). It was originally isolated from the hypothalamus and characterized by Guillemin et al. (U.S. Pat. No. 3,904,594) and is described in U.S. Pat. No. 3,904,594 (Sep. 9, 1975). Somatostatin is found in the gut, pancreas, in the nervous system, in the various exocrine and endocrine glands through the body and in most organs. In normal subjects somatostatin has a broad spectrum of biological activities. It participates in a large number of biological processes where it has the role of an inhibitory factor. It inhibits the release of insulin, prolactin, glucagon, gastrin, growth hormone, thyroid stimulating hormone, secretin and cholecystokinin. (S. Reichlin: Somatostatin, N.Eng. J. Med., 309,1495 and 1556, 1983.)

The mechanism of action of somatostatin is mediated by high affinity membrane associated receptors. Five somatostatin receptors (SSTR1–5) are known. (Reisine, T; Bell, G.I; Endocrine reviews, 1995, 16, 427–42.) All five receptors are heterogeneously distributed and pharmacologically distinct. Somatostatin receptors have been found to be over-expressed in a wide range of tumors, those arising in the brain (including meningioma, astrocytoma, neuroblastoma, hypophysial adenoma, paraganglioma, Merkel cell carcinoma, and gliomas), the digestive-pancreatic tract (including insulinoma, gluconoma, AUODoma, VIPoma, and colon carcinoma), lung, thyroid, mammary gland, prostate, lymphatic system (including both Hodgkin's and non-Hodgkin's lymphomas), and ovaries.

One of the most important effects of somatostatin are its growth-inhibiting ability and its capability to influence pathological cell growth. It is well known that it exerts an inhibitory effect on the growth of cancer cells both directly and by its antagonizing action on growth factors associated with malignant growth. (A. V. Schally: Cancer. Res., 48, 6977, (1988); Taylor, et. al., Biochem., Biophys. Res. Commun., 153, 81 (1988). It has been shown by recent investigations that somatostatin and some somatostatin analogues are capable of activating the tyrosine phosphatase enzyme which antagonizes the effect of tyrosine kinases playing a very important role in the tumorous transformation (A. V. Schally: Cancer Res. 48, 6977 (1988)). The importance of tyrosine kinases is supported by the fact that the majority of oncogenes code for tyrosine kinase and the major part of growth factor receptors is tyrosine kinase (Yarden et al.: Ann. Rev. Biochem. 57, 443 (1989)).

Native somatostatin has a very short or transient effect in vivo since it is rapidly inactivated by endo- and exopeptidases. A large number of novel analogues have been synthesized in order to increase its plasma half life and biological activity. Most of the active analogues contain a disulphide bond and a peptide chain shorter than the original one. The first cyclic hexapeptide showing the whole effects of somatostatin was synthesized by Veber et al. (Nature, 292, 55 (1981)). Newer and more effective cyclic hexa- and octapeptides have been synthesized which possess the whole spectrum of effects of somatostatin (Veber et al.; Life Sci. 34, 1371 (1984); Murphy et al.; Biochem. Biophys. Res. Commun. 132, 922 (1985); Cai et al.; Proc. Natl. Acad. Sci. USA 83, 1896 (1986)).

In spite of the high rates of over expression of somatostatin receptors on a variety of tumors, somatostatin analogues have not gained widespread clinical application for the control of cancer. Their current clinical application is primarily in the control of symptoms associated with metastatic carcinoid or VIP-secreting tumors. The somatostatin analogues have a wide therapeutic index and seem to be free of major side effects. Most of the side effects are gastrointestinal in nature and include minor nausea, bloating, diarrhea, constipation, or steatorrhea. Part of the reason for the restricted clinical use may be due to the need for long-term maintenance therapy, the consequent high cost of such therapy, and the variable effects observed in clinical settings.

Some somatostatin analogues, preparation of such analogues, and uses for such analogues are known in the prior art. Such analogues are used in the treatment of certain cancers and other conditions. One commercially available product, octreotide, D-Phe-Cys-Phe-D-Trp-Lys-Thr-Cys-Thr-of (SEQ ID NO.: 1) (disulphide bridge between the Cys residue), manufactured by Sandoz, and sold under the trade name Sandostatin, is being used clinically to inhibit tumor growth and as a diagnostic agent to detect somatostatin receptor expressing tumors. Of the five receptor sub-types, octreotide and other clinically used somatostatin analogs interact significantly with three of the receptor sub-types, SSTR2, SSTR3 and SSTRS. SSTR2 and SSTRS have recently been reported to mediate anti-proliferative effects of somatostatin on tumor cell growth, and may therefore mediate the effects of octreotide in humans.

A wide variety of somatostatin analogues have been developed. These include RC-160, a potent somatostatin analogue originally synthesized by a team at Tulane University headed by Andrew V. Schally (Cai R. Z., Szoke B., Lu E., Fu D., Redding T. W. and Schally A. V.: Synthesis and biological activity of highly potent octapeptide analogues of somatostatin. Proc Natl Acad Sci USA, 83:1896–1900, 1986). In recent studies conducted by Schally, among others, the effectiveness of RC-160 in inhibiting the growth of humor glioblastomas in vitro and in vivo has been demonstrated (Pinski J, Schally A V, Halmos G, Szepeshazi K and Groot K: Somatostatin analogues and bombesin/gastrin-releasing peptide antagonist RC-3095 inhibit the growth of human glioblastomas in vitro and in vivo. Cancer Res 54:5895–5901, 1994).

Recent patents that describe somatostatin analogs for treatment of cancer are following:

U.S. Pat. No. 6,025,372 (February 2000)
WO 0006185A2 (February 2000)
WO 9922735A1 (May 1999)
WO 9845285A1 (October 1998)
WO 9844921A1 (October 1998)
WO 9844922A1 (October 1998)
U.S. Pat. No. 5,753,618 (May 1998)
U.S. Pat. No. 5,597,894 (January 1997)
EP 0344297E 1 (May 1994)

JP 5124979A (May 1993)

U.S. Pat. No. 4,904,642 (February 1990)

The aim of the present invention is to synthesize novel somatostatin analogs showing a more advantageous and more selective biological action in comparison to that of known compounds. The invention is based on the use of α, α-dialkylated amino acids in the octapeptide analog of somatostatin at position 6. These amino acids are known for inducing conformational constraint. The design of conformationally constrained bioactive peptide derivatives has been one of the most widely used approaches for the development of peptide-based therapeutic agents. Non-standard amino acids with strong conformational preferences may be used to direct the course of polypeptide chain folding, by imposing local stereochemical constraints, in de novo approaches to peptide design. The conformational characteristics of α, α-dialkylated amino acids have been well studied. The incorporation of these amino acids restricts the rotation of Φ, Ψ angles, within the molecule, thereby stabilizing a desired peptide conformation. The prototypic member of α, α-dialkylated aminoacids, α-aminoisobutyric acid (Aib) or α, α-dimethylglycine has been shown to induce β-turn or helical conformation when incorporated in a peptide sequence (Prasad, B. V. V. and Balaram, P. CRC Crit Rev. Biochem. 16,307–347 (1984), Karle, L L. and Balaram, P. Biochemistry 29, 6747–6756, (1990)). The conformational properties of the higher homologs of α, α-dialkylated amino acids such as di-ethylglycine (Deg), di-n-propylglycine (Dpg) and di-n-butylglycine (Dbg) as well as the cyclic side chain analogs of α, α-dialkylated amino acids such as 1-aminocyclopentane carboxylic acid (Ac5c), 1-aminocyclohexane carboxylic acid (Ac6c), 1-aminocycloheptane carboxylic acid (Ac7c) and 1-aminocyclooctane carboxylic acid (Ac8c) have also been shown to induce folded conformation (Prasad, S. et al., Biopolymers 35, 11–20 (1995); Karle, 30 LL. et al., J. Amer. Chem.Soc. 117, 9632–9637(1995)). α, α-Dialkylated amino acids have been used in the design of highly potent chemotactic peptide analogs (Prasad, S. et al., Int. J. Peptide Protein Res. 48, 312–318, (1996)).

The present invention exploits the conformational properties of α, α-dialkylated amino acids for the design of biologically active peptide derivatives, taking somatostatin as the model system under consideration. The invention is directed to somatostatin analogs containing α, α-dialkylated amino acids. A further object of the invention is the synthesis of somatostatin analogs containing α, α-dialkylated amino acids. The inventors have also synthesized peptide derivatives having N-terminal alkanoyl groups of from C2 to C18 carbon atoms, which retain anticancer activity. A still further object of the invention is the preparation of the analogs by solid phase peptide synthesis methodology. It has been shown that lipophilazation of bioactive peptides improves their stability, bioavailability and the ability to permeate biomembranes (Dasgupta, P. et al.; 1999, Pharmaceutical Res. 16, 1047–1053; Gozes, I. et al., 1996, Proc. Natl. Acad. Sci.USA, 93, 427–432).

Throughout the specification and claims, the following abbreviations are used with following meanings:

BOP: Benzotriazole-1-yl-oxy-tris-(dimethylamino)-phosphonium hexofluorosphospate PyBOP: Benzotriazole-1-yl-oxy-tris-pyrrolidino-phosphonium hexofluorophospate HBTU: O-Benzotriazole-N,N,N',N'-tetramethyl-uronium-hexofluoro-phosphate TBTU: 2-(1H-Benzotriazole-1yl)-1,1,3,3-tetramethyluronium tetrafluoroborate HOBt: 1-Hydroxy Benzotriazole DCC: Dicyclohexyl carbodiimide DIPCDI: Diisopropyl carbodiimide DIEA: Diisopropyl ethylamine DMF: Dimethyl formamide DCM: Dichloromethane NMP: N-Methyl-2-pyrrolidinone TFA: trifluoroacetic acid In formula (I) below and throughout the specification, and claims the amino acids residues are designated by their standard abbreviations. Amino acids denote L-configuration unless otherwise indicated by D or DL appearing before the symbol and separated from it by hyphen.

The following abbreviations are used for noncommon amino acids:

Orn=Ornithine

Pen=Penicillamine

Aib=α-Aminoisobutyric acid

Deg=α, α-Di-ethyl glycine

Dpg=α, α-Di-n-propyl glycine

Ac5c=1-Aminocyclopentane carboxylic acid

SUMMARY OF THE INVENTION

The present invention comprises polypeptides of the following formula (I),

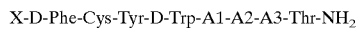

wherein

X is Acetyl or straight, branched, or cyclic alkanoyl group from 3 to 18 carbon atoms, or is deleted;

A1=Orn or Lys;

A2=Aib, Deg, Dpg or Ac5c;

A3=Pen or Cys; or a hydrolyzable carboxy protecting group; or a pharmaceutically acceptable salt of the peptide.

BRIEF DESCRIPTION OF THE FIGURES

FIG. 1 shows the antitumor effect of somatostatin analogs on PTC xenografts.

DETAILED DESCRIPTION OF THE INVENTION

The present invention comprises polypeptides of the following formula (I),

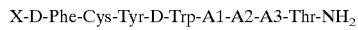

wherein

X is Acetyl or straight, branched, or cyclic alkanoyl group from 3 to 18 carbon atoms, or is deleted;

A1=Orn or Lys;

A2=Aib, Deg, Dpg or Ac5c;

A3=Pen or Cys; or a hydrolyzable carboxy protecting group; or a pharmaceutically acceptable salt of the peptide.

A hydrolyzable carboxy protecting group are those groups which on hydrolysis converts to carboxylic group such as —$CONH_2$, —COOMe, etc. In the case of somatostatin analogs of this invention the carboxylic group is of the Thr amino acid.

Preferably the alkyl portion of the alkanoyl group has 2 to 12 carbon atoms. Preferred alkanoyl groups are acetyl, butanoyl, octanoyl, lauroyl, myristoyl, palmitoyl, n-hexanoyl, isohexanoyl, cyclohexanoyl, cyclopentylcarbonyl, heptanoyl, decanoyl, n-undecanoyl, and 3,7-dimethyloctanoyl.

Salts encompassed within the term "pharmaceutically acceptable salts" refer to non-toxic salts of the compounds of this invention. Representative salts and esters include the following:

acetate, ascorbate, benzenesulfonate, benzoate, bicarbonate, bisulfate, bitartrate, borate, camsylate, carbonate, citrate, dihydrochloride, methanesulfonate, ethanesulfonate, ρ-toluenesulfonate, cyclohexylsulfamate, quinate, edetate, edisylate, estolate, esylate, fumarate, gluconate, glutamate, glycerophophates, hydrobromide, hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, steaxate, succinates, sulfate, sulfamate, subacetate, succinate, tannate, tartrate, tosylate, trifluoroacetate, and valerate.

Other salts include Ca, Li, Mg, Na, and K salts; salts of amino acids such as lysine or arginine; guanidine, diethanolamine or choline; ammonium, substituted ammonium salts or aluminum salts.

The salts are prepared by conventional methods.

In the formula given above, there is a disulphide bond between the two Cys residues or between Cys and Pen residues to indicate cyclization; in all of the compounds of the invention there is such cyclization, but the Cys-Cys bond or Cys-Pen bond lines are omitted for convenience. In other words there is a disulphide bond between $Cys^2$ and A3.

The present invention also envisages pharmaceutical compositions comprising the polypeptides described above and processes for their preparation. These peptides are agonist to somatostatin and somatostatin related peptides and are useful in the prevention and treatment of malignant diseases.

The preferred novel somatostatin analogs of the present invention are as follows:

D-Phe-Cys-Tyr-D-Trp-Orn-Deg-Pen-Thr-$NH_2$ (SEQ ID: 2)

D-Phe-Cys-Tyr-D-Trp-Orn-Ac5c-Pen-Thr-$NH_2$ (SEQ ID: 3)

D-Phe-Cys-Tyr-D-Trp-Orn-Deg-Cys-Thr-$NH_2$ (SEQ ID: 4)

D-Phe-Cys-Tyr-D-Trp-Orn-Ac5c-Cys-Thr-$NH_2$ (SEQ ID: 5)

D-Phe-Cys-Tyr-D-Trp-Lys-Ac5c-Pen-Thr-$NH_2$ (SEQ ID: 6)

D-Phe-Cys-Tyr-D-Trp-Lys-Ac5c-Cys-Thr-$NH_2$ (SEQ ID: 7)

D-Phe-Cys-Tyr-D-Trp-Lys-Aib-Pen-Thr-$NH_2$ (SEQ ID: 8)

D-Phe-Cys-Tyr-D-Trp-Orn-Aib-Pen-Thr-$NH_2$ (SEQ ID: 9)

D-Phe-Cys-Tyr-D-Trp-Orn-Aib-Cys-Thr-$NH_2$ (SEQ ID: 10)

D-Phe-Cys-Tyr-D-Trp-Lys-Deg-Cys-Thr-$NH_2$ (SEQ ID: 11)

D-Phe-Cys-Tyr-D-Trp-Lys-Deg-Pen-Thr-$NH_2$ (SEQ ID: 12)

D-Phe-Cys-Tyr-D-Trp-Orn-Dpg-Pen-Thr-$NH_2$ (SEQ ID: 13)

D-Phe-Cys-Tyr-D-Trp-Orn-Dpg-Cys-Thr-$NH_2$ (SEQ ID: 14)

Acetyl-D-Phe-Cys-Tyr-D-Trp-Orn-Deg-Pen-Thr-$NH_2$ (SEQ ID: 15)

Butanoyl-D-Phe-Cys-Tyr-D-Trp-Orn-Deg-Pen-Thr-$NH_2$ (SEQ ID: 16)

Octanoyl-D-Phe-Cys-Tyr-D-Trp-Orn-Deg-Pen-Thr-$NH_2$ (SEQ ID: 17)

The novel compounds of the present invention have important pharmacological applications. They are potent anti-neoplastic agents and thereby possess therapeutic potential in a number of human cancers.

Pharmaceutical compositions suitable for use in present invention include compositions wherein the active ingredients are contained in an effective amount to achieve its intended purpose.

The term "an effective amount" means that amount of a drug or pharmaceutical agent that will elicit the biological or medical response of a tissue system, animal or human that is being sought.

Suitable routes of administration are those known in the art and include oral, rectal, transdermal, vaginal, transmucosal, or intestinal administration; parenteral delivery, including intramuscular, subcutaneous, intradedullary injections, as well as intrathecal, direct intraventricular, intravenous, intraperitoneal, intransal, or intraocular injections.

In addition to the active ingredients, these pharmaceutical compositions may contain suitable pharmaceutically acceptable carriers excipients, diluents, solvents, flavorings, colorants etc. The preparations may be formulated in any form including but not limited to tablets, dragees, capsules, powders, syrups, suspensions, slurries, time released formulations, sustained release formulations, pills, granules, emulsions, patches, injections, solutions, liposomes and nanoparticles.

The exact formulation, route of administration and dosage can be chosen by the individual physician in view of the patient's condition.

Toxicity and therapeutic efficacy of the peptides of this invention can be determined by standard pharmaceutical procedures in cell cultures or experimental animals.

Synthesis of Peptides

The novel peptide analogs embodied in the present invention contain amino acids, namely α, α-dialkylated amino acids, which are known to induce highly specific constraints in the peptide backbone. The α, α-dialkylated amino acids were synthesized from the appropriate ketones. These ketones were first converted into their corresponding hydantoins, which on hydrolysis with strong acid or alkali such as $H_2SO_4$, HCl, NaOH and $Na_2CO_3$ gave the respective amino acids. In a preferred embodiment of the invention, 60% sulphuric acid is employed as the hydrolyzing agent.

The novel peptides of the present invention can be made by exclusively, solid phase techniques, by a combination of solution phase procedures and solid phase techniques, or, by fragment condensation. These methods for the chemical synthesis of polypeptides are well known in the art (Stewart and Young, Solid Phase Peptide Synthesis, W. H. Freeman & Co., 1969). Preferred, semi-automated, stepwise solid phase methods for synthesis of peptides of the invention are provided in the examples discussed in a subsequent section of this document.

In a preferred embodiment of the present invention the peptides were synthesized using Fmoc strategy, either manually, or on a semi-automatic peptide synthesizer (CS Bio, Model 536), using optimum side chain protection. The peptides were assembled from C-terminus to N-terminus. Peptides amidated at the carboxyterminus were synthesized using the Rink Amide resin. The loading of the first Fmoc protected amino acid was achieved via an amide bond formation with the solid support, mediated by Diisopropylcarbodiimide (DIPCDI) and HOBt. Substitution levels for automated synthesis were preferably between 0.2 and 0.8 mmole amino acid per gram resin. The steps involved in the synthesis of the somatostatin analogs employed the following protocol:

TABLE I

| STEP | REAGENT | MIX TIME (MIN) | NO OF CYCLES |
|---|---|---|---|
| 1. | Methylene chloride | 1 | 2 |
| 2. | Dimethyl formamide | 1 | 1 |
| 3. | 20% Piperidine in Dimethyl formamide | 1 | 1 |
| 4. | 20% Piperidine in Dimethyl formamide | 29 | 1 |
| 5. | Dimethyl formamide | 1 | 3 |
| 6. | Isopropanol | 1 | 2 |
| 7. | Methylene chloride | 1 | 2 |
| 8. | Amino Acid Variable | Variable | 1 |
| 9. | Dimethyl formamide | 1 | 2 |
| 10. | Stop or Return for next cycle | | |

The resin employed for the synthesis of carboxy-terminal amidated peptide analogs was 4-(2',4'-Dimethoxyphenyl-Fmoc-aminomethyl)-phenoxymethyl derivatized polystyrene 1% divinylbenzene (Rink Amide) resin (100–200 mesh), procured from Advanced Chemtech, Louisville, Ky., U.S.A., (0.7 milliequivalent $NH_2$/g resin).

In a particularly preferred embodiment of the present invention the following chemical moieties were used to protect reactive side chains of the peptides during the synthesis procedure:

The N-terminal amino group was protected by 9-fluorenylmethoxycarbonyl (Fmoc) group. The tryptophan residue was either left unprotected or used with Boc protection. The side chain amino group of Lysine and Ornithine was protected using Boc group, preferably. Threonine and Tyrosine residues were used with t-Butyl (t-Bu) protection. Trityl or Acetamidomethyl (Acm) were the preferred protecting groups for Cysteine and Penicillamine was preferably protected with the Acetamidomethyl (Acm) group.

In a preferred embodiment of the invention, 2–8 equivalents of Fmoc protected amino acid per resin nitrogen equivalent was used. The activating reagents used for coupling amino acids to the resin, in solid phase peptide synthesis, are well known in the art. These include DCC, DIPCDI, DIEA, BOP, PyBOP, HBTU, TBTU, and HOBt. Preferably, DCC or DIPCDI/HOBt or HBTU/HOBT and DIEA were used as activating reagents in the coupling reactions. The protected amino acids were either activated in situ or added in the form of pre-activated esters known in the art such as NHS esters, Opfp esters etc. Atherton, E. et al. 1988, J. Chem. Soc. Perkin. Traps. L, 2887; Bodansky, M. In "The Peptides, Analysis, Synthesis and Biology" (E. Gross, J., Melenhofer eds) Vol. 1, Academic Press, New York, 1979, 106. The coupling reaction was carried out in DMF, DCM or NMP or a mixture of these solvents and was monitored by Kaiser test [Kaiser et al., Anal. Biochem., 34, 595–598 (1970)]. In case of a positive Kaiser test, the appropriate amino acid was re-coupled using freshly prepared activated reagents.

After the assembly of the peptide chain was completed, disulfide bond formation was either carried out on-resin, where the Acm side-chain protecting groups were removed using Iodine in Dimethylformamide, and the free thiol groups thus generated were oxidized simultaneously to yield the cyclized peptide. This was followed by the removal of the amino-terminal Fmoc group using steps 1–6 of the above protocol. The peptide-resin was then washed with methanol and dried. Where post-cleavage disulphide formation was carried out, the N-terminal Fmoc group was removed and the peptide was cleaved from the resin support by treatment with a cleavage mixture consisting of trifluoroacetic acid, crystalline phenol, thioanisole, ethanedithiol and de-ionized water for 1 to 4 hours at room temperature. Normally, the cleavage mixture also simultaneously removed the side-chain protecting groups, except for the side-chain protecting Acm groups that were not removed by the above procedure. The crude peptide was obtained by precipitation with cold dry ether, filtered, dissolved, and lyophilized. Where disulfide formation was carried out on the crude Acm-protected peptide, the Acm group was removed by any of the known methods such as using Thallium trifluoroacetate, iodine etc.

The resulting crude peptide was purified by preparative high performance liquid chromatography (HPLC) using a LiChroCART® $C_{18}$ (250. Times. 10) reverse phase column (Merck, Darmstadt, Germany) on a Preparative HPLC system (Shimadzu Corporation, Japan) using a gradient of 0.1% TFA in acetonitrile and water. The eluted fractions were reanalyzed on Analytical HPLC system (Shimadzu Corporation, Japan) using a $C_{18}$ LiChrospher®, WP-300 (300 X 4) reverse-phase column. Acetonitrile was evaporated and the fractions were lyophilized to obtain the pure peptide. The identity of each peptide was confirmed by mass spectra.

The present invention will be further described in detail with reference to the following examples, as will be appreciated by a person skilled in the art, is merely illustrative, and should not be construed as limiting. Various other modifications of the invention will be possible without departing from the spirit and scope of the present invention.

EXAMPLE 1

Synthesis of SEQ ID NO: 2

D-Phe-Cys-Tyr-D-Trp-Orn-Deg-Pen-Thr-$NH_2$

First Loading on Rink Amide Resin

A typical preparation of the Fmoc-Thr-Rink Amide Resin was carried out using 0.5 g of 4-(2',4'-Dimethoxyphenyl-Fmoc-aminomethyl)phenoxymethyl-derivatized polystyrene 1% divinylbenzene (Rink Amide) resin, (0.7 milliequivalent $NH_2$/g resin), (100–200 mesh), procured from Advanced Chemtech, Louisville, Ky., U.S.A. Swelling of the resin was typically carried out in dichloromethane measuring to volumes 10–40 ml/g resin. The resin was allowed to swell in methylene chloride (2×25 ml, for 10 min.). It was washed once in dimethyl-formamide (DMF) for 1 min. All solvents in the protocol were added in 20 ml portions per cycle. The Fmoc-protecting group on the resin was removed by following steps 3–7 in the protocol. The deprotection of the Fmoc group was checked by the presence of blue beads in Kaiser test. For loading of the first amino acid on the free amino ($NH_2$) group of the resin, the first amino acid was weighed in three to six fold excess in the amino acid vessel of the peptide synthesizer. This was dissolved in dimethyl-formamide (A.C.S. grade) (J. T. Baker, Phillipsburg, N.J., U.S.A.) and activated with DIPCDI, just prior to the addition to the resin in the reaction vessel of the peptide synthesizer. For difficult couplings, alternative BOP/DIEA, HBTU/DIEA couplings were carried out. The coupling reaction was carried out for a period ranging from 1–3 hours. The loading of the amino acid on the resin was confirmed by the presence of colorless beads in the Kaiser Test. Recoupling was carried out for incomplete reactions. The loading efficiency was ascertained by the increase of weight of the resin after the addition of the amino acid.

The peptide sequence was assembled by subsequent deprotection and coupling cycles, as mentioned earlier in the protocol.

The synthesis of SEQ ID NO: 2 was started on 0.5 g scale. Upon completion of synthesis and removal of the N-terminal Fmoc protecting group (steps 1–6 of the synthesis cycle), the peptide-resin was washed twice with methanol, dried and weighed to obtain 0.694 g. This was subjected to cleavage in a cleavage mixture consisting of trifluoroacetic acid and scavengers, ethanedithol and water for a period of 1.5–5 hours at room temperature with continuous stirring. The peptide was precipitated using cold dry ether to obtain 172 mg of the crude peptide. Disulfide bond formation in the crude peptide was carried out in iodine in methanol (3× to 12× molar excess of iodine for 5 min. to 1 hr.) and excess of iodine was removed with sodium thiosulfate or ascorbic acid or extraction with $CCl_4$ after evaporation of methanol on rotavapour.

The crude, cyclized peptide was purified on a $C_{18}$ preparative reverse phase HPLC column (250×10) on a gradient system comprising acetonitrile and water in 0.1% TFA as described previously. The prominent peak was collected and lyophilized, reanalysed on analytical HPLC and subjected to mass spectrometry. There was a good agreement between the observed molecular weight and calculated molecular weight (Calculated mass is ~1073; Observed Mass=1074.1). The pure peptide was then used for bioassay.

EXAMPLE 2

Synthesis of Analog: SEQ ID NO: 3

D-Phe-Cys-Tyr-D-Trp-Orn-Ac5c-Pen-Thr-$NH_2$

On a 0.5 g scale of resin, 0.698 of peptide-resin was obtained post-deprotection of the N-terminal Fmoc group. After cleavage and lyophilization, 236 mg of the crude peptide was obtained. Disulfide formation and purification steps were carried out as in the examples above. The calculated mass of the pure peptide was ~1071 and the observed mass was 1073.1.

EXAMPLE 3

Synthesis of Analogy: SEQ ID NO: 4

D-Phe-Cys-Tyr-D-Trp-Orn-Deg-Cys-Thr-$NH_2$

On 0.5 g scale of resin, 0.632 g of peptide-resin was obtained post-deprotection of the N-terminal Fmoc group. After cleavage and lyophilization, 268 mg of the crude peptide was obtained. Disulfide formation and purification steps were carried out as in the examples above. The calculated mass of the pure peptide was ~1045 and the observed mass was 1047.1.

EXAMPLE 4

Synthesis of Analog: SEQ ID NO: 5

D-Phe-Cys-Tyr-D-Trp-Orn-Ac5c-Cys-Thr-$NH_2$

On 0.5 g scale of resin, 0.685 g of peptide-resin was obtained post-deprotection of the N-terminal Fmoc group. After cleavage and lyophilization, 326 mg of the crude peptide was obtained. Disulfide formation and purification steps were carried out as in the examples above. The calculated mass of the pure peptide was ~1043 and the observed mass was 1044.8.

EXAMPLE 5

Synthesis of Analog: SEQ ID NO: 6

D-Phe-Cys-Tyr-D-Trp-Lys-Ac5c-Pen-Thr-$NH_2$

On 0.5 g scale of resin, 0.794 g of peptide-resin was obtained post-deprotection of the N-terminal Fmoc group. After cleavage and lyophilization, 288 mg of the crude peptide was obtained. Disulfide formation and purification steps were carried out as in the examples above. The calculated mass of the pure peptide was ~1086 and the observed mass was 1087.2.

EXAMPLE 6

Synthesis of Analog: SEQ ID NO: 7

D-Phe-Cys-Tyr-D-Trp-Lys-Ac5c-Cys-Thr-$NH_2$

On 0.5 g scale of resin, 0.770 g of peptide-resin was obtained post-deprotection of the N-terminal Fmoc group. After cleavage and lyophilization, 268 mg of the crude peptide was obtained. Disulfide formation and purification steps were carried out as in the examples above. The calculated mass of the pure peptide was ~1058 and the observed mass was 1059.0.

EXAMPLE 7

Synthesis of Analogy: SEQ ID NO: 9

D-Phe-Cys-Tyr-D-Trp-Orn-Aib-Pen-Thr-$NH_2$

On 0.5 g scale of resin, 0.747 g of peptide-resin was obtained post-deprotection of the N-terminal Fmoc group. After cleavage and lyophilization, 218 mg of the crude peptide was obtained. Disulfide formation and purification steps were carried out as in the examples above. The calculated mass of the pure peptide was ~1046 and the observed mass was 1047.2.

EXAMPLE 8

Synthesis of Analogy: SEQ ID NO: 10

D-Phe-Cys-Tyr-D-Trp-Orn-Aib-Cys-Thr-$NH_2$

On 0.5 g scale of resin, 0.762 g of peptide-resin was obtained post-deprotection of the N-terminal Fmoc group. After cleavage and lyophilization, 325 mg of the crude peptide was obtained. Disulfide formation and purification steps were carried out as in the examples above. The calculated mass of the pure peptide was ~1018 and the observed mass was ~1019.4.

EXAMPLE 9

Synthesis of Analog: SEQ ID NO: 14

D-Phe-Cys-Tyr-D-Trp-Orn-Dpg-Cys-Thr-$NH_2$

On 0.5 g scale of resin, 0.752 g of peptide-resin was obtained post-deprotection of the N-terminal Fmoc group. After cleavage and lyophilization, 339 mg of the crude peptide was obtained. Disulfide formation and purification steps were carried out as in the examples above. The calculated mass of the pure peptide was ~1074 and the observed mass was 1075.0.

EXAMPLE 10

The cytotoxic effect of peptides SEQ ID NO: 2, SEQ ID NO: 3, SEQ ID NO: 6, and SEQ ID NO: 9, was studied by MTT assay which is based on the principle of uptake of MTT [3-[4,5-dimethylthiazol-2-yl]-2,5-diphenyl tetrazolium bromide], a tetrazolium salt by the metabolically active cells where it is metabolized by active mitochondria into a blue colored formazan product which can be read spectrophotometrically. Briefly, tumor cells PTC (primary human colon cancer cell line), KB (Oral squamous), U87MG (Glioblastoma), HBL100 (Breast), HeP2 (Laryngeal), ECV304 (Endothelial), PA-1 (Ovary) and L132 (Lung) were incubated with the peptide analogs for 48 hours at 37° C. in a 96-well culture plate, followed by the addition of 100 μg MTT and further incubation of 1 hour. The formazan crystals formed inside the cells were dissolved with a detergent comprising 10% Sodium dodecyl sulfate and 0.01 N HCl and optical density read on a multiscan ELISA reader. The optical density was directly proportional to the number of proliferating and metabolically active cells. Percent cytotoxicity of peptide analogs is shown in the following tables.

| Cell Line | Percentage cytotoxicity at different concentrations | | | |
|---|---|---|---|---|
| | 1 μM | 100 nM | 10 nM | 1 nM |
| SEQ ID NO: 2 | | | | |
| PTC | 9.0 ± 3.2 | 20 ± 1.5 | 14 ± 2.9 | 40 ± 0.5 |
| KB | 12.0 ± 4.3 | 19.0 ± 5.2 | 34.9 ± 4.6 | 28.0 ± 3.2 |
| U87MG | 33.9 ± 1.2 | 39.5 ± 1.4 | 41.9 ± 2.4 | 22.8 ± 3.5 |
| HBL100 | 10.6 ± 1.4 | 15.7 ± 3.5 | 22.8 ± 1.8 | 19.4 ± 4.5 |
| HeP2 | 10.0 ± 2.4 | 13.0 ± 3.5 | 29.7 ± 4.4 | 14.9 ± 3.2 |
| L132 | 17.7 ± 5.5 | 22.8 ± 4.6 | 23.4 ± 4.2 | 12.7 ± 2.9 |
| PA-1 | 12.8 ± 3.3 | 22.9 ± 2.3 | 27.9 ± 3.4 | 29.5 ± 24 |
| ECV304 | 6.0 ± 2.9 | 14.9 ± 2.9 | 19.8 ± 3.3 | 22.8 ± 3.9 |
| SEQ ID NO: 3 | | | | |
| PTC | 13 ± 2.3 | 13 ± 1.3 | 11 ± 0.8 | 15 ± 1.5 |
| KB | 17.9 ± 1.3 | 19.4 ± 5.2 | 25.0 ± 4.6 | 29.8 ± 1.2 |
| U87MG | 28.9 ± 1.2 | 42.4 ± 1.4 | 45.0 ± 2.4 | 44.2 ± 3.5 |
| HBL100 | 10.6 ± 1.4 | 11.8 ± 3.2 | 17.5 ± 2.8 | 14.6 ± 4.5 |
| HeP2 | 10.0 ± 2.4 | 25.8 ± 2.5 | 26.8 ± 4.4 | 13.9 ± 3.6 |
| L132 | 19.8 ± 5.5 | 25.9 ± 2.6 | 28.6 ± 4.2 | 19.0 ± 2.2 |
| PA-1 | 19.5 ± 3.3 | 38.5 ± 2.2 | 39.5 ± 3.4 | 29.5 ± 1.0 |
| ECV304 | 14.9 ± 1.6 | 15.9 ± 2.9 | 23.9 ± 1.3 | 13.9 ± 3.9 |
| SEQ ID NO: 6 | | | | |
| PTC | 9 ± 2.1 | 8 ± 5.2 | 11 ± 7.1 | 12 ± 1.5 |
| KB | 12.9 ± 1.1 | 19.0 ± 5.2 | 23.0 ± 4.8 | 28.0 ± 1.2 |
| U87MG | 39.5 ± 1.2 | 42.9 ± 1.4 | 40.4 ± 2.4 | 39.0 ± 3.5 |
| HBL100 | 8.0 ± 1.4 | 12.6 ± 3.2 | 14.5 ± 2.8 | 15.7 ± 4.5 |
| HeP2 | 10.6 ± 2.4 | 11.0 ± 2.5 | 14.8 ± 4.4 | 8.0 ± 3.6 |
| L132 | 13.7 ± 5.8 | 22.9 ± 2.6 | 25.7 ± 4.8 | 14.9 ± 1.2 |
| PA-1 | 8.0 ± 3.3 | 22.6 ± 2.2 | 25.9 ± 1.4 | 19.4 ± 1.0 |
| ECV304 | 7.9 ± 1.6 | 13.9 ± 2.9 | 24.9 ± 3.8 | 18.9 ± 3.9 |
| SEQ ID NO: 9 | | | | |
| KB | 12.0 ± 1.2 | 18.0 ± 5.2 | 27.0 ± 4.8 | 28.0 ± 1.6 |
| U87MG | 42.9 ± 1.2 | 53.3 ± 1.4 | 29.7 ± 2.4 | 13.9 ± 2.5 |
| HBL100 | 7.9 ± 1.2 | 14.9 ± 2.2 | 23.9 ± 4.4 | 26.9 ± 2.6 |
| HeP2 | 19.9 ± 2.4 | 27.9 ± 2.5 | 21.4 ± 4.4 | 15.6 ± 3.6 |
| L132 | 12.9 ± 1.8 | 22.8 ± 2.6 | 26.1 ± 4.8 | 14.9 ± 2.6 |
| PA-1 | 16.6 ± 3.1 | 22.7 ± 2.2 | 12.8 ± 1.4 | 4.6 ± 1.0 |
| ECV304 | 12.9 ± 1.6 | 19.9 ± 2.6 | 23.9 ± 3.1 | 18.0 ± 2.9 |

EXAMPLE 11

In vivo Antitumor Activity of the Novel Synthesized Somatostatin Analogs on Primary Tumor (Colon) Xenografted Mice The antitumor activity of SEQ ID NO:2 and SEQ ID NO:3 was studied in human colon adenocarcinoma (PTC) xenografts in nude mice. PTC tumor xenografts were grown in Balb/c athymic mice by subcutaneous inoculation of a single cell suspension of PTC cells ($15 \times 10^6$ cells/100 μl). The tumor bearing animals were divided into 3 groups of three animals each including one group comprising untreated control animals. Treatment with novel somatostatin analogs was initiated when the average tumor volumes, as measured using a vernier caliper, were between 400–800 mm$^3$. Solutions of SEQ ID NO:2 and SEQ ID NO:3 were prepared at a concentration of 85 μg/ml and intravenously administered to the assigned group of tumor bearing animals at a dose of 8.5 μg/100 μl twice a day so that the total dose of 17 g/day was administered to each animal. The treatment was continued for a period of 10 days.

The antitumor activity of the compounds was monitored by measuring tumor volumes every fourth day using the formula W*W*L*0.04 (W=smaller diameter, L=larger diameter). The percentage inhibition of tumor growth was calculated using the formula (1-tumor volume-treated/tumor volume control)* 100. The following table shows the tumor volumes (mm$^3$) of individual tumor bearing animals measured till day 21 in the treated and untreated animals. FIG. 1 shows the tumor kinetics till day 21 in the treated and untreated animals. The peptides showed a significant antitumor activity on PTC xenografts. The percentage inhibition of tumor growth caused by SEQ ID NO: 2 and SEQ ID NO:3 peptide as compared to controls on day 21 was 57.1% and 54.7% 5 respectively.

| Days | SEQ ID NO: 2 | | | | | SEQ ID NO: 3 | | | | |
|---|---|---|---|---|---|---|---|---|---|---|
| | IV | V | VI | Avg | S.D. | I | II | III | Avg | S.D. |
| 0 | 0 | 0 | 0 | 0 | 0 | 0 | 0 | 0 | 0 | 0 |
| 9 | 480 | 678 | 806 | 654 | 164 | 560 | 774 | 324 | 552 | 225 |
| 13 | 1254 | 2196 | 2333 | 1927 | 587 | 1946 | 1800 | 1530 | 1758 | 211 |
| 18 | 1965 | 5240 | 4453 | 3886 | 1709 | 3177 | 3610 | 4234 | 3674 | 531 |
| 21 | 491 | 4839 | 6250 | 3860 | 3001 | 0 | 4939 | 7301 | 4080 | 3725 |

All publications referenced are incorporated by reference herein, including the amino acid sequences listed in each publication. All the compounds disclosed and referred to in the publications mentioned above are incorporated by reference herein, including those compounds disclosed and referred to in articles cited by the 10 publications mentioned.

What is claimed is:

1. A peptide of the formula:

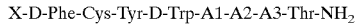

X-D-Phe-Cys-Tyr-D-Trp-A1-A2-A3-Thr-NH$_2$ wherein

X is acetyl or straight, branched, or cyclic alkanoyl group of from 3 to 18 carbon atoms, or is deleted;

A1 is Orn or Lys;

A2 is Aib, Deg, Dpg or Ac5c;

A3 is Pen or Cys or a hydrolyzable carboxy protecting group; or pharmaceutically acceptable salt thereof.

2. A peptide according to claim 1, wherein the alkyl portion of the alkanoyl group is from 2 to 12 carbon atoms.

3. The peptide of claim 1, wherein X is deleted and A1 is Orn, A2 is Deg and A3 is Pen; and the peptide is D-Phe-Cys-Tyr-D-Trp-Orn-Deg-Pen-Thr-NH$_2$ (SEQ ID NO: 2).

4. The peptide claim 1, wherein X is deleted and A1 is Orn, A2 is Ac5c and A3 is Pen; and the peptide is D-Phe-Cys-Tyr-D-Trp-Orn-Ac5c-Pen-Thr-NH$_2$ (SEQ ID NO: 3).

5. The peptide of claim 1, wherein X is deleted and A1 is Orn, A2 is Deg and A3 is Cys; and the said peptide is D-Phe-Cys-Tyr-D-Trp-Orn-Deg-Cys-Thr-NH$_2$ (SEQ ID NO: 4).

6. The peptide of claim 1, wherein X is deleted and A1 is Orn, A2 is AcSc and A3 is Cys; and the peptide is D-Phe-Cys-Tyr-D-Trp-Orn-AcSc-Cys-Thr-NH$_2$ (SEQ ID NO: 5).

7. The peptide of claim 1, wherein X is deleted and A1 is Lys, A2 is Ac5c and A3 is Pen; and the peptide is D-Phe-Cys-Tyr-D-Trp-Lys-Ac5c-Pen-Thr-NH$_2$ (SEQ ID NO: 6).

8. The peptide of claim 1, wherein X is deleted and A1 is Lys, A2 is Ac5c and A3 is Cys; and the peptide is D-Phe-Cys-Tyr-D-Trp-Lys-Ac5c-Cys-Thr-NH$_2$ (SEQ ID NO: 7).

9. The peptide of claim 1, wherein X is deleted and A1 is Lys, A2 is Aib and A3 is Pen; and the peptide is D-Phe-Cys-Tyr-D-Trp-Lys-Aib-Pen-Thr-NH$_2$ (SEQ ID NO: 8).

10. The peptide claim 1, wherein X is deleted and A1 is Orn, A2 is Aib and A3 is Pen; and the peptide is D-Phe-Cys-Tyr-D-Trp-Orn-Aib-Pen-Thr-NH$_2$ (SEQ ID NO: 9).

11. The peptide claim 1, wherein X is deleted and A1 is Orn, A2 is Aib and A3 is Cys; and the peptide is D-Phe-Cys-Tyr-D-Trp-Orn-Aib-Cys-Thr-NH$_2$ (SEQ ID NO: 10).

12. The peptide of claim 1 wherein X is deleted and A1 is Lys, A2 is Deg and A3 5 is Cys; and the peptide is D-Phe-Cys-Tyr-D-Trp-Lys-Deg-Cys-Thr-NH$_2$ (SEQ ID NO: 11).

13. The peptide of claim 1, wherein X is deleted and A1 is Lys, A2 is Deg and A3 is Pen; and the peptide is D-Phe-Cys-Tyr-D-Trp-Lys-Deg-Pen-Thr-NH$_2$ (SEQ ID NO: 12).

14. The peptide of claim 1, wherein X is deleted and A1 is Orn, A2 is Dpg and A3 is Pen; and the peptide is D-Phe-Cys-Tyr-D-Trp-Orn-Dpg-Pen-Thr-NH$_2$ (SEQ ID NO: 13).

15. The peptide of claim 1, wherein X is deleted and A1 is Orn, A2 is Dpg and A3 is Cys; and the peptide is D-Phe-Cys-Tyr-D-Trp-Orn-Dpg-Cys-Thr-NH$_2$ (SEQ ID NO: 14).

16. The peptide of claim 1, wherein X is acetyl and A1 is Orn, A2 is Deg and A3 is Pen; and the peptide is Acetyl-D-Phe-Cys-Tyr-D-Trp-Orn-Deg-Pen-Thr-NH$_2$ (SEQ ID NO: 15).

17. The peptide of claim 1, wherein X is butanoyl and A1 is Orn, A2 is Deg and A3 is Pen; and the peptide is Butanoyl-D-Phe-Cys-Tyr-D-Trp-Orn-Deg-Pen-Thr-NH$_2$ (SEQ ID NO: 16).

18. The peptide of claim 1, wherein X is octanoyl and A1 is Orn, A2 is Deg and A3 is Pen; and the peptide is Octanoyl-D-Phe-Cys-Tyr-D-Trp-Orn-Deg-Pen-Thr-NH$_2$ (SEQ ID NO: 17).

19. A solid phase synthesis process for the preparation of a peptide analog of formula (I):

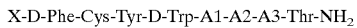

X-D-Phe-Cys-Tyr-D-Trp-A1-A2-A3-Thr-NH$_2$ wherein

X is acetyl or straight, branched, or cyclic alkanoyl group of from 3 to 18 carbon atoms, or is deleted;

A1 is Orn or Lys;

A2 is Aib, Deg, Dpg or Ac5c;

A3 is Pen or Cys;

which comprises sequentially loading protected α-α-dialkylated amino acids in sequential cycles to the amino terminus of a solid phase resin, coupling the amino acids to assemble a peptide-resin assembly, removing the protecting groups and cleaving the peptide from the resin to obtain a peptide analog.

20. The process as claimed in claim 19, wherein said α-α-dialkylated amino acid is protected at its α-amino groups by a 9-fluorenyl methoxy carbonyl (Fmoc) group.

21. The process as claimed in claim 19, wherein the coupling is carried out in the presence of activated agents selected from the group consisting of DCC, DIPCDI, DIEA, BOP, PyBOP, HBTU, TBTU, and HOBt.

22. The process as claimed in claim 19, wherein the coupling is carried out in the presence of a solvent selected from the group consisting of DMF, DCM, and NMP or a mixture thereof.

23. The process as claimed in claim 19, wherein said peptide is cleaved from said peptide-resin assembly by treatment with trifluoroacetic acid, crystalline phenol, thioanisole, ethanedithiol and water for 1.5 to 5 hours at room temperature.

24. A composition comprising an effective amount of a polypeptide according to claim 1, and a pharmaceutically acceptable carrier.

25. A method of treatment of cancer in mammals which comprises the administration of an effective amount of polypeptide according to claim 1.

26. A method according to claim 20 further comprising administering a chemotherapeutic compound.

* * * * *

```
                        SEQUENCE LISTING

<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp

<400> SEQUENCE: 1

Xaa Cys Phe Xaa Lys Thr Cys Thr
  1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = alpha, alpha-di-ethyl glycine = Deg
<221> NAME/KEY: MOD_RES
<222> LOCATION: (7)
<223> OTHER INFORMATION: /product = penicillamine/label = Pen

<400> SEQUENCE: 2

Xaa Cys Tyr Xaa Xaa Xaa Xaa Thr
  1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = 1-Aminocyclopentane carboxylic
      acid/label = Ac5c
```

```
<221> NAME/KEY: MOD_RES
<222> LOCATION: (7)
<223> OTHER INFORMATION: /product = Penicillamine/label = Pen

<400> SEQUENCE: 3

Xaa Cys Tyr Xaa Xaa Xaa Xaa Thr
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = alpha,alpha-Di-ethyl glycine = Deg

<400> SEQUENCE: 4

Xaa Cys Tyr Xaa Xaa Xaa Cys Thr
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = 1-Aminocyclopentane carboxylic
      acid/label = Ac5c

<400> SEQUENCE: 5

Xaa Cys Tyr Xaa Xaa Xaa Cys Thr
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label - D-Phe
<221> NAME/KEY: MOD_RES
<222> LOCATION: (4)
<223> OTHER INFORMATION: /product = D-tryptophan/label = D-Trp
<221> NAME/KEY: MOD_RES
```

```
<222> LOCATION: (6)
<223> OTHER INFORMATION: /product = 1-Aminocyclopentane carboxylic
      acid/label = Ac5c
<221> NAME/KEY: MOD_RES
<222> LOCATION: (7)
<223> OTHER INFORMATION: /product = Penicillamine/label = Pen

<400> SEQUENCE: 6

Xaa Cys Tyr Xaa Lys Xaa Xaa Thr
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (6)
<223> OTHER INFORMATION: /product = 1-Aminocyclopentane carboxylic
      acid/label = Ac5c

<400> SEQUENCE: 7

Xaa Cys Tyr Xaa Lys Xaa Cys Thr
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (6)
<223> OTHER INFORMATION: /product = alpha-aminoisobutyric
      acid/label = Aib
<221> NAME/KEY: MOD_RES
<222> LOCATION: (7)
<223> OTHER INFORMATION: /product = Penicillamine/label = Pen

<400> SEQUENCE: 8

Xaa Cys Tyr Xaa Lys Xaa Xaa Thr
 1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
```

```
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = alpha-aminoisobutyric
      acid/label = Aib
<221> NAME/KEY: MOD_RES
<222> LOCATION: (7)
<223> OTHER INFORMATION: /product = Penicillamine/label = Pen

<400> SEQUENCE: 9

Xaa Cys Tyr Xaa Xaa Xaa Xaa Thr
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = alpha-aminoisobutyric
      acid/label = Aib

<400> SEQUENCE: 10

Xaa Cys Tyr Xaa Xaa Xaa Cys Thr
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:
      This peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (6)
<223> OTHER INFORMATION: /product = alpha,alpha-diethyl
      glycine/label = Deg

<400> SEQUENCE: 11

Xaa Cys Tyr Xaa Lys Xaa Cys Thr
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
```

```
<222> LOCATION: (4)
<223> OTHER INFORMATION: /product = D-tryptophan/label = D-Trp
<221> NAME/KEY: MOD_RES
<222> LOCATION: (6)
<223> OTHER INFORMATION: /product = alpha, alpha-di-ethyl
      glycine/label = Deg
<221> NAME/KEY: MOD_RES
<222> LOCATION: (7)
<223> OTHER INFORMATION: /product = Penicillamine/label =Pen

<400> SEQUENCE: 12

Xaa Cys Tyr Xaa Lys Xaa Xaa Thr
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = alpha,
      alpha-di-n-propylglycine/label = Dpg
<221> NAME/KEY: MOD_RES
<222> LOCATION: (7)
<223> OTHER INFORMATION: /product = Penicillamine/label = Pen

<400> SEQUENCE: 13

Xaa Cys Tyr Xaa Xaa Xaa Xaa Thr
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:
      This peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product =
      alpha,alpha-di-n-propylglycine/label = Dpg

<400> SEQUENCE: 14

Xaa Cys Tyr Xaa Xaa Xaa Cys Thr
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:
      This peptide was synthetically generated.
```

```
<221> NAME/KEY: MOD_RES
<222> LOCATION: (1)
<223> OTHER INFORMATION: /product = Acetyl- D-phenylalanine/label =
      Acetyl-D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = alpha,alpha-di-ethyl
      glycine/label = Deg
<221> NAME/KEY: MOD_RES
<222> LOCATION: (7)
<223> OTHER INFORMATION: /product = Penicillamine/label = Pen

<400> SEQUENCE: 15

Xaa Cys Tyr Xaa Xaa Xaa Xaa Thr
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:
      This peptide was synthetically generated.
<221> NAME/KEY: MOD_RES
<222> LOCATION: (1)
<223> OTHER INFORMATION: /product = Butanoyl-D-phenylalanine/label
      =Butanoyl- D-Phe
<221> NAME/KEY: MOD_RES
<222> LOCATION: (4)
<223> OTHER INFORMATION: /product = D-tryptophan/label = D-Trp
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = alpha,alpha-di-ethyl
      glycine/label = Deg
<221> NAME/KEY: MOD_RES
<222> LOCATION: (7)
<223> OTHER INFORMATION: /product = Penicillamine/label = Pen

<400> SEQUENCE: 16

Xaa Cys Tyr Xaa Xaa Xaa Xaa Thr
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product =Octanoyl- D-phenylalanine/label =
      Octanoyl-D-Phe
<221> NAME/KEY: MOD_RES
<222> LOCATION: (4)
<223> OTHER INFORMATION: /product = D-tryptophan/label = D-Phe
<221> NAME/KEY: MOD_RES
<222> LOCATION: (5)
<223> OTHER INFORMATION: /product = Ornithine/label = Orn
<221> NAME/KEY: MOD_RES
<222> LOCATION: (6)
<223> OTHER INFORMATION: /product = alpha,alpha-Di-ethyl
      glycine/label = Deg
<221> NAME/KEY: MOD_RES
```

```
<222> LOCATION: (7)
<223> OTHER INFORMATION: /product = Penicillamine/label = Pen

<400> SEQUENCE: 17

Xaa Cys Tyr Xaa Xaa Xaa Xaa Thr
 1               5
```